United States Patent [19]

Seifert et al.

[11] Patent Number: 5,714,059
[45] Date of Patent: Feb. 3, 1998

[54] FLOW UNIT FOR FERROGRAPHIC ANALYSIS

[75] Inventors: William W. Seifert, Wellesley Hills; Vernon C. Westcott, Lincoln; John B. Desjardins, Clinton, all of Mass.

[73] Assignee: Institute Guilfoyle, Belmont, Mass.

[21] Appl. No.: 552,994

[22] Filed: Nov. 3, 1995

[51] Int. Cl.⁶ .................................................. G01N 21/05
[52] U.S. Cl. .......................... 210/94; 210/222; 210/450; 356/246
[58] Field of Search .......................... 210/95, 222, 450, 210/94; 209/223.1, 232; 277/9.5, 10; 356/244, 246; 422/102

[56] References Cited

U.S. PATENT DOCUMENTS

| | | | |
|---|---|---|---|
| 2,464,628 | 3/1949 | Willard | 209/232 |
| 3,261,086 | 7/1966 | Dunn | 277/10 |
| 3,352,197 | 11/1967 | Porges et al. | 210/94 |
| 4,405,235 | 9/1983 | Rossiter | 356/246 |
| 5,053,344 | 10/1991 | Zborowski et al. | 436/177 |

*Primary Examiner*—Matthew O. Savage
*Attorney, Agent, or Firm*—Cesari and McKenna, LLP

[57] ABSTRACT

A flow unit especially useful for closed-channel Ferrographic analysis comprises a glass substrate, a plastic platen, and an elastomeric gasket sheet disposed between them. Holes in the gasket sheet form flow chambers. Opposite free ends of the gasket sheet extend beyond the edges of the substrate and of the platen so as to allow pulling the ends in opposite directions parallel to the surface of the substrate and thereby shearing the bond between the substrate and the gasket.

22 Claims, 9 Drawing Sheets

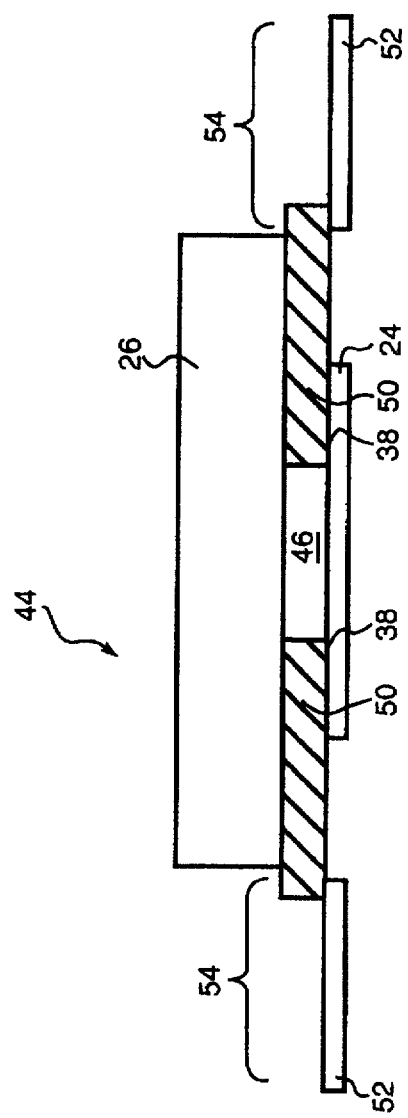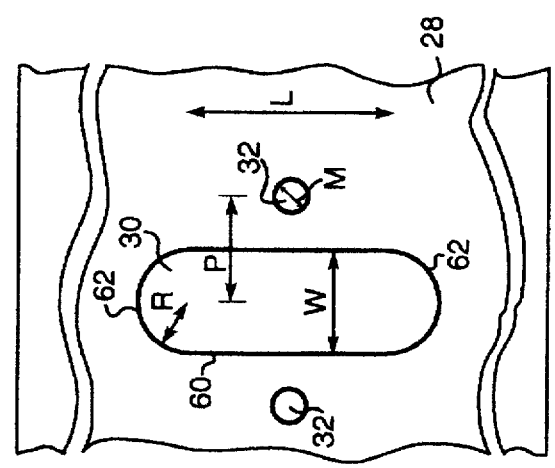

FLOW UNIT FOR FERROGRAPHIC ANALYSIS

FIELD OF THE INVENTION

This invention relates to the reversible joining of a glass substrate to an elastomeric material. Particularly, it relates to a technique for forming a flow chamber having a thin glass wall and disassembling the chamber without damaging the glass substrate.

BACKGROUND OF THE INVENTION

Ferrography is a method of separating suspended particles from a liquid. The interaction between a magnetic field through which the particles move and the magnetic dipole moments of the particles causes the particles to deposit onto a substrate in the region of strongest field gradient. This technique has been applied to removing wear particles from used lubricating oil and depositing them onto a microscope slide for analysis.

Cell sorting techniques exploiting differences in surface protein compositions of biological cells find wide application in research and in diagnostic procedures relating to cancer and immunodeficiency diseases, as well as in other biomedical applications. Ferrographic techniques can be applied to this type of analysis based on the ability of different surface protein compositions to be marked with magnetic tags. For example, after magnetic tagging, lymphocytes may be readily sorted Ferrographically. This approach to cell sorting efficiently concentrates the cells of interest and thus does not necessitate sophisticated fluidic or optical systems for subsequent study of counting of the cells.

U.S. Pat. No. 5,053,344 discloses an "Analytical Ferrograph" adapted for magnetic cell deposition. It employs a magnet having pole members that define an interpolar gap therebetween with a relatively high magnetic flux density. For Ferrographic analysis of biological cells suspended in a fluid, an aliquot of the fluid is pumped through a "closed" flow chamber, which is part of a larger flow unit, disposed in the fringing magnetic field. Opposing parallel plates define the fluid pathway in the flow chamber, which is mounted with one of its sides, the substrate, against the pole members and over the gap. Particles that are magnetically susceptible (either naturally or due to prior preparation) are separated from the balance of the fluid, and are deposited onto a deposition surface, i.e., the interior surface of the substrate. After the entire aliquot has passed through the flow chamber, the flow unit is disassembled and the deposit is analyzed.

Optimal performance of such a system depends, in part, on the features of the flow chamber. Typically, the substrate onto which the cells are deposited is a slide, such as of common borosilicate glass. The optical transparency, mechanical rigidity, smooth surface, and low chemical reactivity of glass facilitate analysis of the deposit after removal of the flow chamber from the apparatus. Also, it is often desirable that the substrate be very thin in order for the deposition surface to be as close as possible to the interpolar gap; under this arrangement, tagged cells in the fluid flowing adjacent the gap encounter strong field gradients which efficiently draw the cells to the surface, where they are deposited in compact, well-defined regions. If, instead, the deposition surface is relatively far from the gap, fewer cells are drawn to the surface and the pattern formed by the deposited cells is more diffuse.

A flow chamber configuration that allows the formation of several parallel flow chambers within a single flow unit allows simultaneous processing of several aliquots under identical flow and magnetic field conditions. Collection of the resulting deposits in compact form on a single deposition surface facilitates comparison of different deposits derived from the same sample. In such a configuration, the integrity of the seal around each deposition chamber is crucial for preventing cross-contamination. Fluid entrainment in the vicinity of the seal is also of concern. Any fluid trapped within the unit may contact the cells deposited on the substrate when the flow unit is disassembled, and any resulting smearing could hinder accurate analysis of the deposit.

Finally, hygienic considerations require that all of these attributes be embodied in a flow chamber that is disposable after a single use. This prerequisite imposes an economic constraint on the range of materials and subsequent processing appropriate for constructing the flow chamber.

Although Ferrography effectively separates lymphocytes, several shortcomings in implementation of the flow unit, related to the aforementioned requirements, have limited its practicality. For example, in one realization, the individual fluid pathways and flow chambers in the flow unit are defined by holes through a spacer sheet, or gasket, of elastomeric material disposed between two plates, one of which is the glass substrate and the other of which is referred to herein as the platen. Pressure applied perpendicularly to the substrate surface maintains the integrity of the seal around each flow chamber. Even in the absence of applied pressure, electrostatic or frictional forces can hold the plates against the spacer sheet, parallel to one another.

However, with known configurations of the flow unit, separation of the gasket from the substrate or the platen after removal of the flow unit from the Ferrograph is problematic. Attempts to peel or lift either of the substrate or gasket from the other expose the substrate to bending moments. A thin glass substrate does not tolerate the bending moments well, and the incidence of breakage—which may render the deposit illegible—is high. Although the susceptibility of the substrate to breakage might be minimized by increasing the thickness of the substrate, this change would move the deposition surface farther away from the interpolar gap, with resulting reduction in the number of cells deposited and diffusion of the deposit.

Another approach has been to define an individual flow chamber by disposing an O-ring in a groove on the surface of a polymeric block, serving as the platen, and pressing the flat surface of the glass substrate against the O-rings. This approach uses a smaller contact area between the elastomeric material and the substrate than with a sheet-like spacer, and so allows easier removal of the substrate from the elastomeric material. However, it has several disadvantages. For small-scale production, the grooves are formed by machining the platen surface. The cost of individually machining each platen may preclude disposal after a single use. Also, the presence of the O-ring promotes entrainment of liquid around the periphery of the flow chamber; when the flow unit is disassembled, droplets of the remaining liquid may disturb the deposit. Finally, the glass substrate in the assembled unit is vulnerable to breakage by any force applied perpendicularly to but nonuniformly over the exterior surface of the substrate. This weakness makes secure packaging of the assembled flow unit difficult and loading as a unit into the apparatus impractical.

DESCRIPTION OF THE INVENTION

Objects of the Invention

It is, accordingly, an object of the invention to provide a flow unit incorporating a thin glass substrate in a manner that enables disassembly of the unit without breaking the substrate.

It is another object of the invention to provide a flow unit having a plurality of mutually liquid-tight flow chambers.

It is another object of the invention to provide a flow unit, all of the parts of which are economically disposable.

It is yet another object of the invention to provide a flow unit that can be handled during storage and after assembly can be loaded onto a magnet assembly without breaking the glass substrate.

Another object of the invention is to provide a flow unit that minimizes liquid entrainment at the peripheries of the flow chambers.

Brief Summary of the Invention

The present invention makes use of a flat elastomeric spacer sheet, hereinafter referred to as a gasket, between the thin glass substrate and the platen. However, unlike prior-art approaches to forming the flow unit, the invention configures the gasket such that free ends of the sheet extend beyond the edges of the substrate and platen so as to allow pulling of at least one of the free ends of the sheet parallel to the plane of the gasket. The resultant stretching of the sheet engenders shear stresses along the interface between the substrate and gasket and thereby shears the gasket-substrate and gasket-platen bonds without subjecting the substrate to any appreciable bending moment. Because of the much greater strength of the substrate in tension, i.e. parallel to its surface, the flow chamber can be disassembled while leaving the substrate, and the cell deposits thereon, intact. Even a very thin glass substrate can be separated from the gasket without breaking; the invention is particularly useful in cases where the glass substrate is thinner than 150 micrometers thick, such as a conventional 100 to 120 micrometers-thick glass slide.

An individual flow chamber is formed by a chamber hole through the gasket; a plurality of such holes creates a plurality of liquid-tight flow chambers capable of simultaneous function without cross-contamination. Optional stress concentration holes through the gasket provide an additional benefit. These holes, located on opposite sides of each chamber hole, cause the sides of the flow chamber to bow outward, away from the cell deposit, when the gasket is stretched. This behavior reduces the risk of disturbing the deposit by a moving contact with the elastomeric material when the latter is stretched to remove the substrate.

The platen used in the flow unit of the invention requires no special surface finishing, and apart from any features required for incorporation into a particular apparatus, such as fluid inlet and outlet ports to permit the passage of fluid through the unit, the platen is a simple block. Also, the planar morphology of the seals does not promote liquid entrainment at the peripheries of the flow chambers.

Thus, the invention allows a Ferrograph, or any technology benefiting from a disposable flow unit having a thin glass wall, to be used to maximum advantage. The design lends itself to packaging of the assembled flow unit for uncomplicated loading into the apparatus. Although the terms "flow unit" and "flow chamber" have been adopted for describing the invention, it is easily conceivable that the invention could be applied to applications that do not require flow through the unit or chamber.

In one embodiment, illustrated hereinbelow, the force required to disengage the substrate from the gasket is minimized by appending sections of lower elasticity material to the elastomeric portion of the gasket, thereby providing relatively rigid end sections of the gasket. This arrangement localizes the stretching of the gasket to the surfaces from which it is to be freed rather than requiring deformation of the entire length of the gasket to achieve the same effect. The rigid sections include the free ends that are gripped during pulling and transmit the forces to the elastomeric portion.

The invention also provides an apparatus, to be illustrated hereinbelow, for removing the substrate from the gasket. One side of a perforated block is in communication with a vacuum chamber. The vacuum transmitted through the block holds the substrate against the opposite side of the block, thereby retaining the flow chamber in position in the apparatus. Two take-up wheels, one for each free end of the gasket, grip the free end portions at points evenly distributed along their entire width in order to apply force uniformly along the width. A crank rotates one or both wheels so as to pull one or both of the ends perpendicularly to the edges and parallel to the surface of the substrate, thus causing the elongated spacing layer to separate from the substrate.

BRIEF DESCRIPTION OF THE DRAWINGS

The foregoing discussion will be understood more readily from the following detailed description of the invention, when taken in conjunction with the accompanying drawings, in which:

FIG. 5 is a cross section of the flow unit of FIG. 4 taken along line 5—5;

FIG. 6 is a plan view of the gasket schematically depicting the dimensions of its features;

It will be appreciated that, for purposes of illustration, these figures are not necessarily drawn to scale.

DETAILED DESCRIPTION OF THE INVENTION

Figure 1:
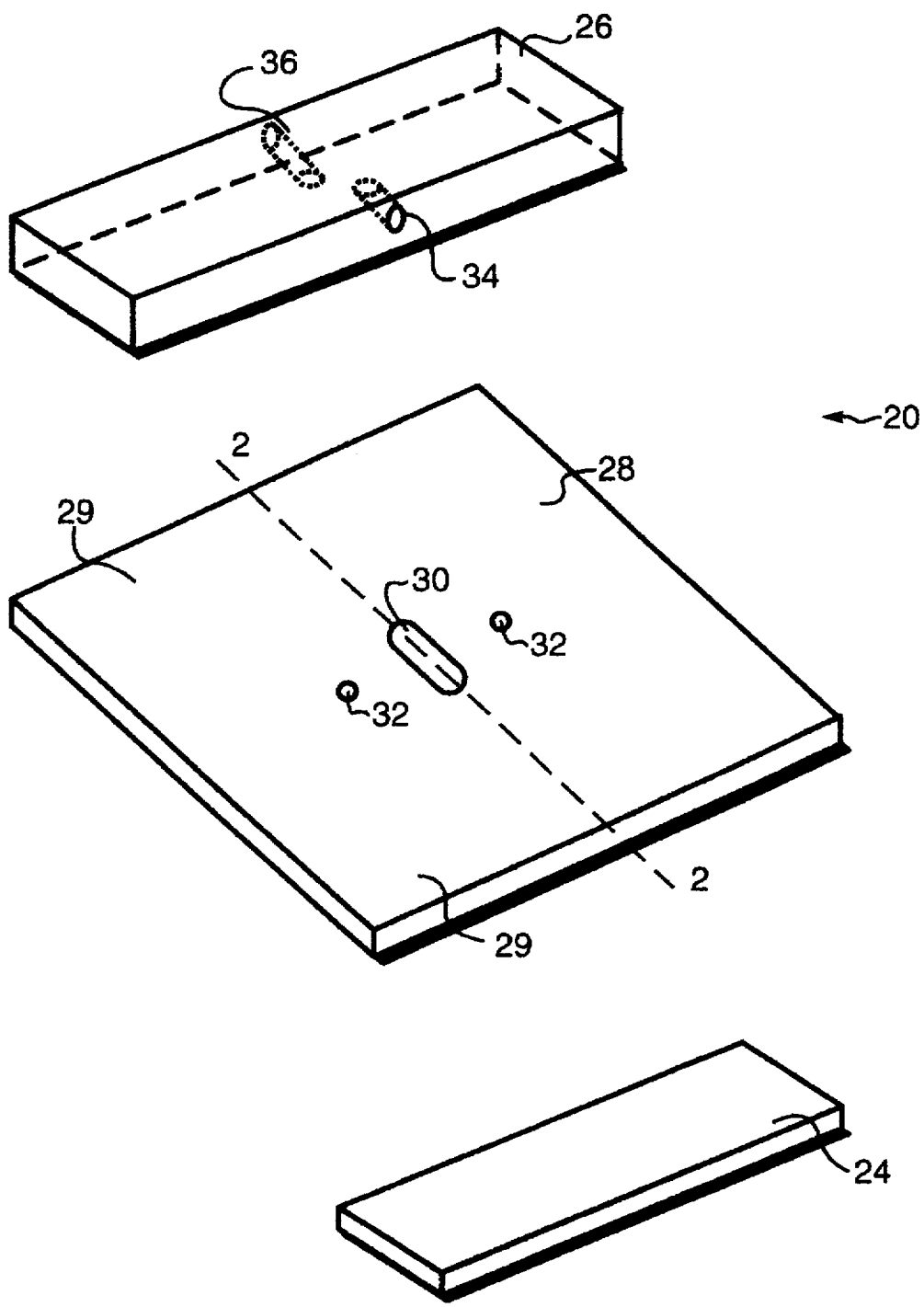
FIG. 1 is an exploded view of a flow unit of the invention.
Figure 2:
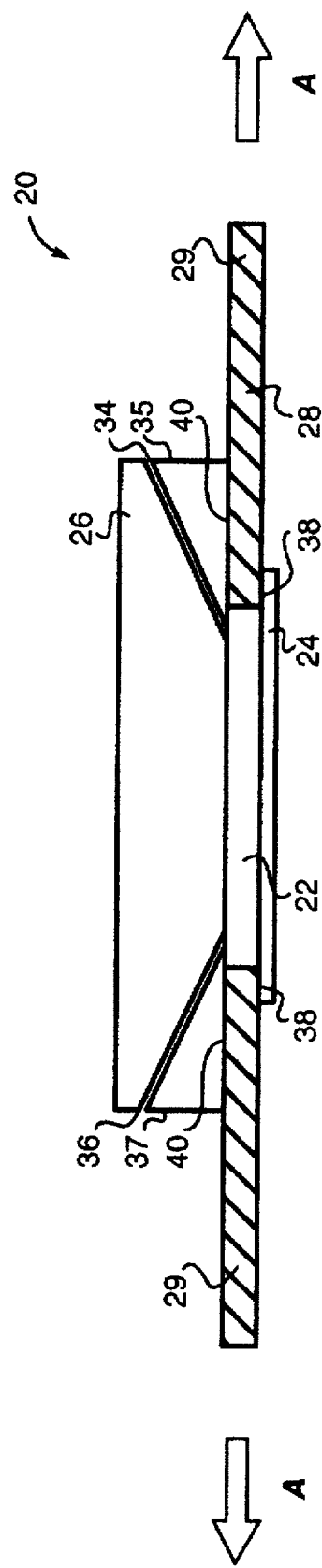
FIG. 2 is a cross section of the assembled flow unit of FIG. 1 taken along line 2—2.

FIGS. 1 and 2 illustrate a flow unit 20 having a single flow chamber 22. The unit 20 comprises three members: a substrate 24 and a platen 26, mutually parallel, and a thin spacer sheet or gasket 28 of an elastomeric polymer interposed between them. The gasket 28 has opposite free ends 29 extending beyond the edges of the substrate 24 and the platen 26. The gasket 28 is continuous except for an elongated chamber hole 30 and optional flanking stress concentration holes 32. Contact between the gasket 28 and both the substrate 24 and the platen 26 seals the chamber hole 30 to form the flow chamber 22. Inlet and outlet channels 34 and 36 extend through the platen 26 into opposite ends 35 and 37, respectively, of the flow chamber 22 to provide for fluid flow through the chamber.

For most applications, the platen 26 is preferably optically transparent and may be of a relatively rigid polymeric material. A thin sheet of glass, such as a microscope cover slip functions well as the substrate 24. The gasket 28 is preferably of a material that electrostatically adheres to the substrate 24 and the platen 26, thereby forming a conformal coating and self-sealing the periphery of the chamber hole 30 upon slightly pressing together the members during assembly of the flow unit 20. It is also desirable that the gasket material not be wet by any fluids to be used in the chamber 22. Silicone rubber and latex rubber have proven suitable materials for the gasket 28. If desired, a thin layer of low-tack adhesive may be applied to the members to promote sealing at the interface 38 between the substrate 24 and the gasket 28 and at the interface 40 between the gasket 28 and the platen 26. The optional application of a slight pressure perpendicular to the plane of the substrate 24 can enhance sealing at the gasket-substrate interface 38 and the gasket-platen interface 40 during use of the flow unit.

The flow unit 20 of the invention is disassembled in the Tensile g manner. Tensile forces are applied to the free ends 29 parallel to the gasket sheet 28, as indicated by the arrows A in FIG. 2. The resultant stretching of the sheet 28 gives rise to shear stresses in the planes of the interfaces 38 and 40 that rupture the gasket-substrate and gasket-platen bonds and allow the substrate to be lifted off the gasket easily. The advantage of the present invention stems from this change, with respect to known techniques, in orientation of the load applied during disassembly.

Figure 3A:
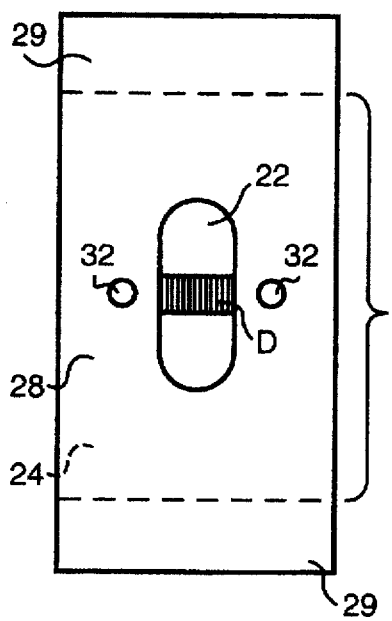
FIGS. 3A and 3B show the elastic behavior of the gasket, FIG. 3A depicting a quiescent gasket and FIG. 3B depicting the same gasket under tensile stress.
Figure 3B:
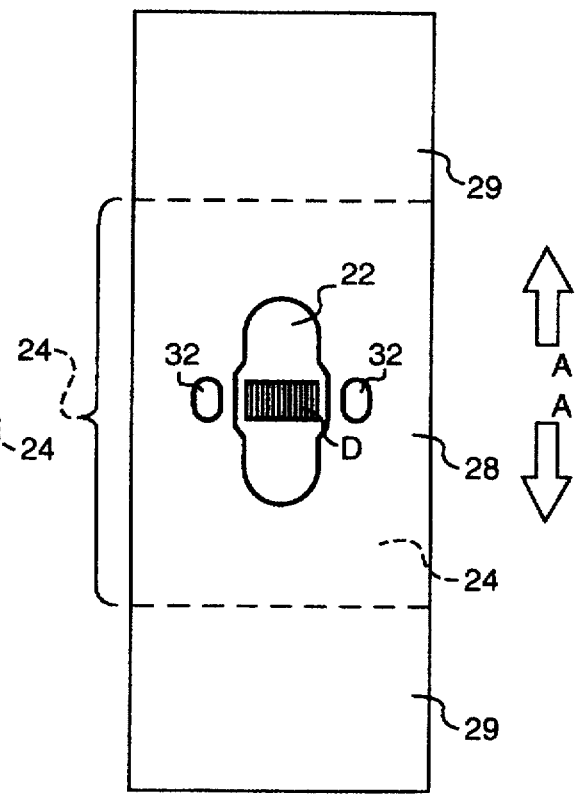

FIGS. 3A and 3B illustrate the function of the stress concentration holes 32. FIG. 3A shows a portion of the gasket 28 over the substrate 24 in the assembled flow unit 20 after use. The flow chamber 22 contains a deposit D on substrate 24. FIG. 3B shows the effect of stressing the gasket 28 by pulling on the free ends 29 as indicated by the arrows A. The flow chamber 22 elongates in the direction of the tensile stress. The stress concentration holes 32 elongate in the same direction with consequent lateral contraction of the portions of gasket 28 between the flow chamber 22 and the holes 32, so that sections of the wall of the flow chamber 22 bow away from the flow chamber interior, and particularly from the deposit D. This motion of the gasket 28 reduces the likelihood that the moving sheet 28 will disturb the deposit D during disassembly.

Figure 4:
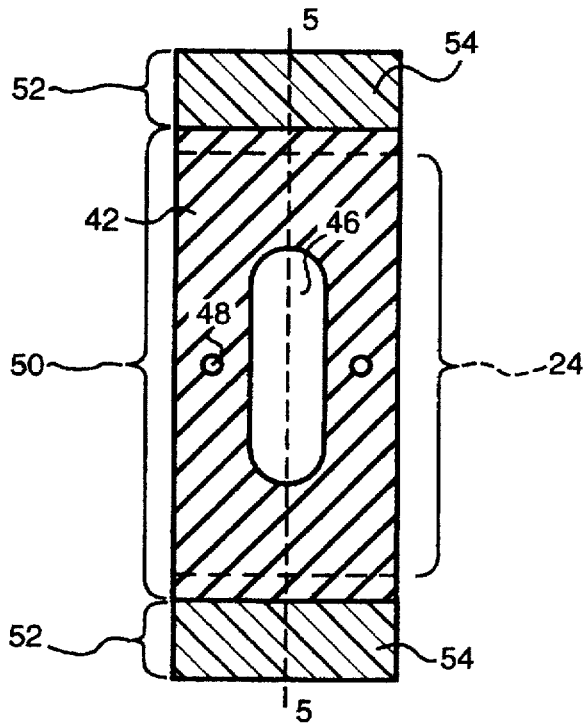
FIG. 4 illustrates the gasket and substrate of an alternate embodiment of the flow unit of the invention.

In an alternate implementation of the invention, shown in FIGS. 4 and 5, a composite gasket 42 is used. The chamber hole forming flow chamber 46 and the stress concentration holes 48 reside in a middle elastomeric section 50 that performs the sealing function and stretches during disassembly. Rigid sections 52 of a stiffer material are attached to the ends of the elastomeric section 50 and serve as the free ends 54. The rigidity of the sections 52 help distribute the stretching force applied during disassembly along the width of the sheet 42. This structure also reduces the amount of stretching required to disassemble the flow unit because only the elastomeric section 50 stretches. Because of the reduced length of elastomer compared to that in a flow unit 20 having an all-elastomeric gasket 28, less energy is required to free the gasket 42 from the substrate 24 and the platen 26.

The dimensions of the flow unit's features are chosen in accordance with the application for which it is designed. For use in a Ferrographic system, these dimensions are selected for compatibility with the structure of the particular Ferrograph and for enhancement the magnetically driven separation. One example of a single-chambered flow unit 20 which can function in a Ferrographic system uses a thin sheet of glass, such as a borosilicate glass microscope cover slip, for the substrate 24. The substrate has thickness of about 100 micrometers, a length of 60 mm, and a width of about 24 mm parallel to the longitudinal axis of the chamber hole 30. The gasket 28 is a 0.5-mm silicone rubber layer and has a length of 14 cm parallel to the axis of the chamber hole 30, and a width of 62 mm. A 1-cm-thick slab of a transparent polymer, having a length of about 12 cm and a width of about 5 cm parallel to the axis of the chamber hole 30, functions as the platen 26. The length of the platen 26 is greater than the width of the gasket 28 in order to facilitate securing the assembled flow unit in the Ferrograph.

The thickness of the flow chamber 22 influences the Reynolds number of the fluid flow in the chamber. The flow chamber 22 is thin, preferably less than about 500 micrometers in thickness so that all the cells passing through the chamber experience a high magnetic field gradient.

With reference to FIG. 6, in the illustrated example of the flow unit 20, the gasket 28 has the hole 30 with width W of 6 mm, straight side walls 60 having length L of 11.5 mm, and semicircular end walls 62 having a radius R of 3 mm. The stress concentration holes 32 have a diameter M of 4 mm. The holes 32 are placed at midlength of the chamber hole 30 and the centers of the holes 32 are separated from the centerline of the hole 30 by a distance P of 6 mm. The platen 26 is placed over the gasket 28 so as to locate the fluid inlet and outlet channels 34 and 36 symmetrically with respect to the length of chamber hole 30 so that sample fluid enters and exits the deposition chamber 22 at short distances from the respective ends of the chamber 22.

Figure 7:
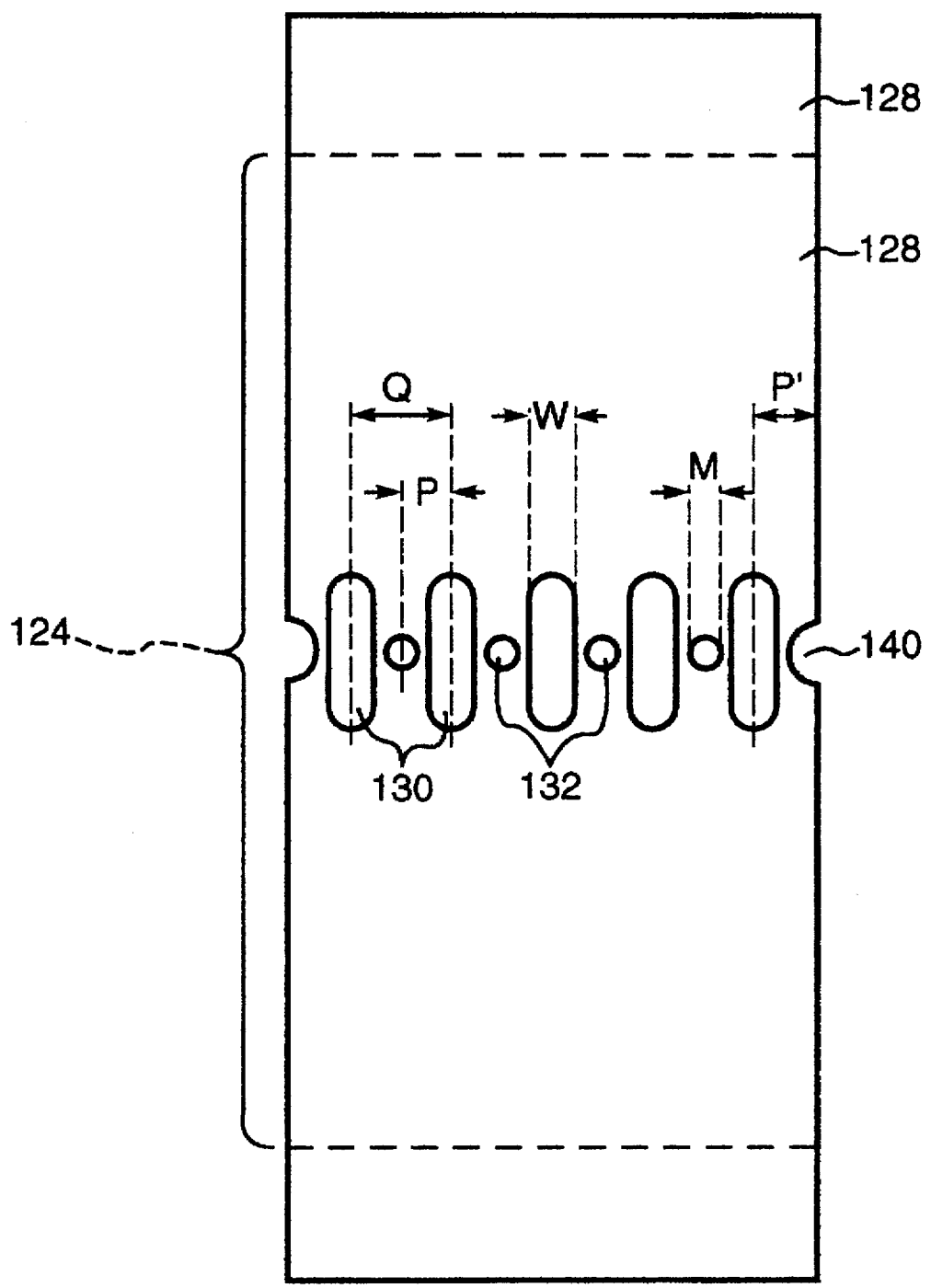
FIG. 7 illustrates the substrate and gasket of a flow unit having multiple parallel elongated chamber holes.

FIG. 7 illustrates another embodiment of the invention in which a flow unit comprises a gasket 128 having a series of five coplanar, parallel chamber holes 130 in accordance with an alterative embodiment of the flow unit having a plurality of flow chambers. The dimensions of the substrate 124, gasket 128, and platen of this flow unit, as well as of the chamber holes 130 and stress concentration holes 132 are the same as those for the corresponding features described above in connection with the flow unit 20, except for the outermost stress concentration holes 140. These latter holes 140 are semicircular with the same radius as the others 132, and their centers are separated from that of the nearest hole 130 by a distance of P' of 7 mm. The center-to-center distance Q of adjacent chamber holes 130 is 12 mm.

Each flow chamber of this embodiment has its own set of inlet and outlet channels, configured as described above in connection with the platen 26, placed at equal intervals along the width of the platen (not shown). During disassembly, the gasket 128 of such a flow unit is stretched in a direction parallel to the longitudinal axes of the chamber holes 130 in order not to disturb any deposits on the substrate 124 by lateral motion of the sheet 128 due to stretching.

Figure 9:
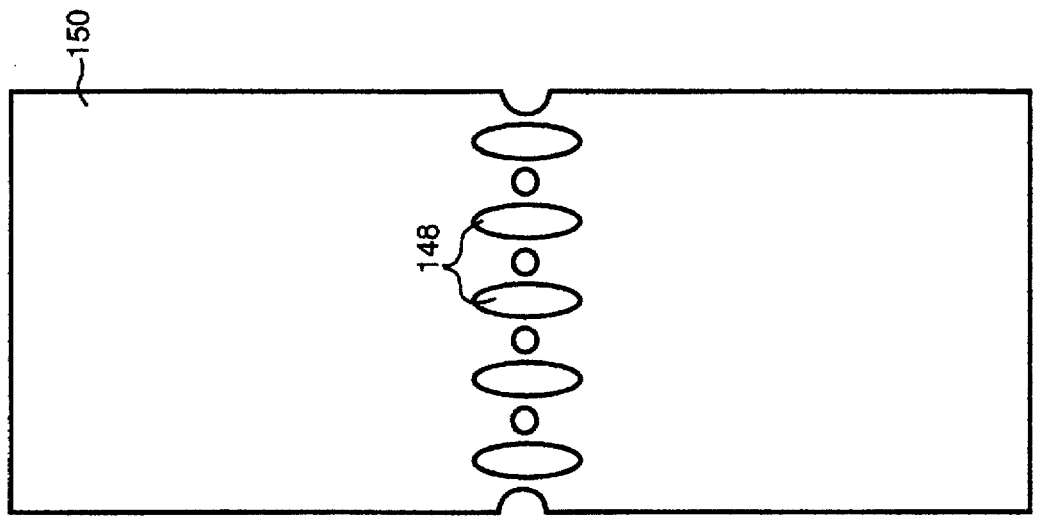
FIG. 9 illustrates a gasket having multiple parallel elliptical chamber holes.
Figure 8:
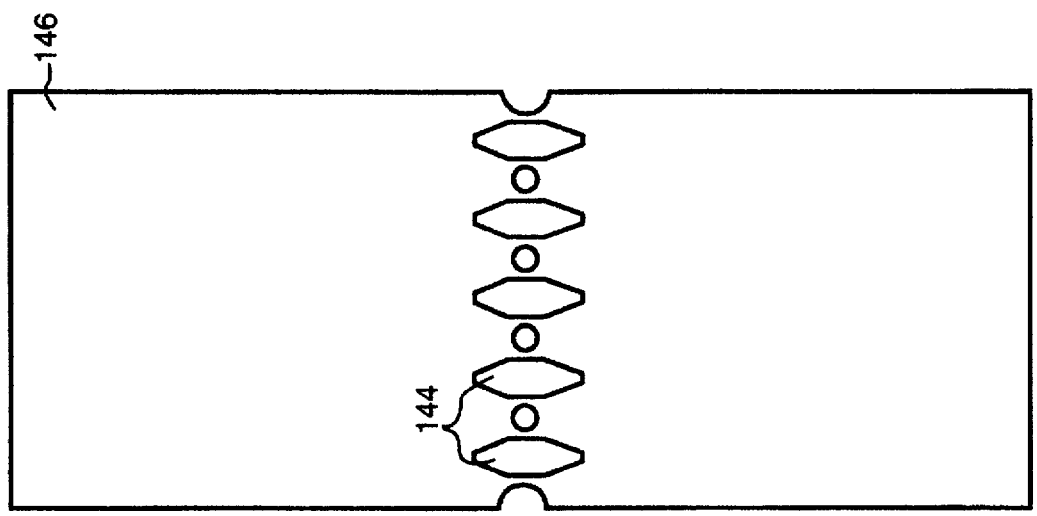
FIG. 8 illustrates a gasket having multiple parallel tapered chamber holes.

With reference to FIGS. 8 and 9, other geometries for the chamber hole 130 of the gasket 128 may be used to advantage. Both the tapered hole 144 of the gasket 146 (FIG. 6) and the elliptical hole 148 of the gasket 150 (FIG. 7) form multi-chambered flow units that have reduced dead volume with respect to the elongated hole 130 of FIG. 7.

Figure 10A:
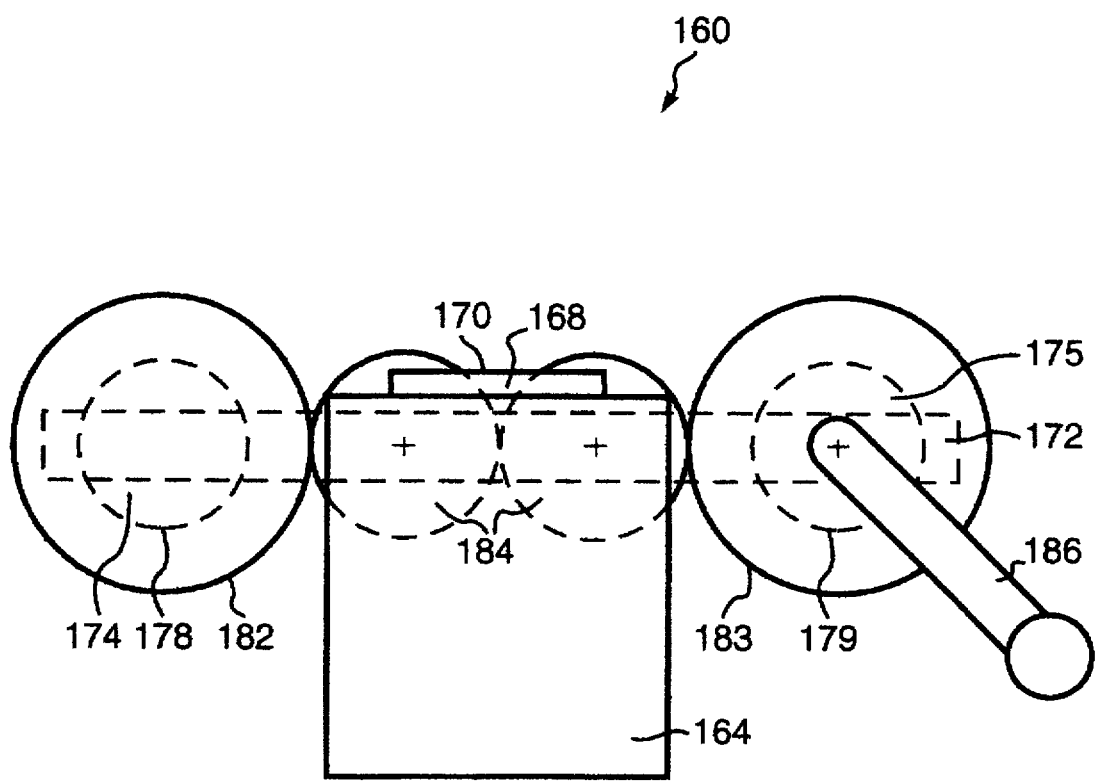
FIGS. 10A and 10B are front views of a stretcher that can be used for disassembling the flow unit of the invention, FIG. 10A showing the stretcher in isolation and FIG. 10B showing the stretcher in use with a flow unit of the invention.

FIG. 10A shows a stretcher 160 for mechanically disassembling flow unit of the invention, such as the flow unit 20 of FIGS. 1 and 2. A vacuum chamber 164, in communication with a vacuum source (not shown), is perforated so as to provide negative pressure to a metal block 168 disposed over the chamber 164. The block 168 has fluid passageways that transmit suction to the top surface 170 of the metal block. A bracket 172 holds take-up wheels 174, 175 rotatably in place on opposite sides of the block 168. Each of take-up wheels 174, 175 has means (not shown), such as a spring-loaded clamp, for holding a free end 29 of the gasket on its respective wheel surface 178, 179. The wheels 174, 175 have gears 182, 183 and are connected to one another by a gear train 184. The gearing is configured as shown so that turning a crank 186 on wheel 175 causes the wheels 174, 175 to rotate in opposite directions through an equal angle.

Figure 10B:
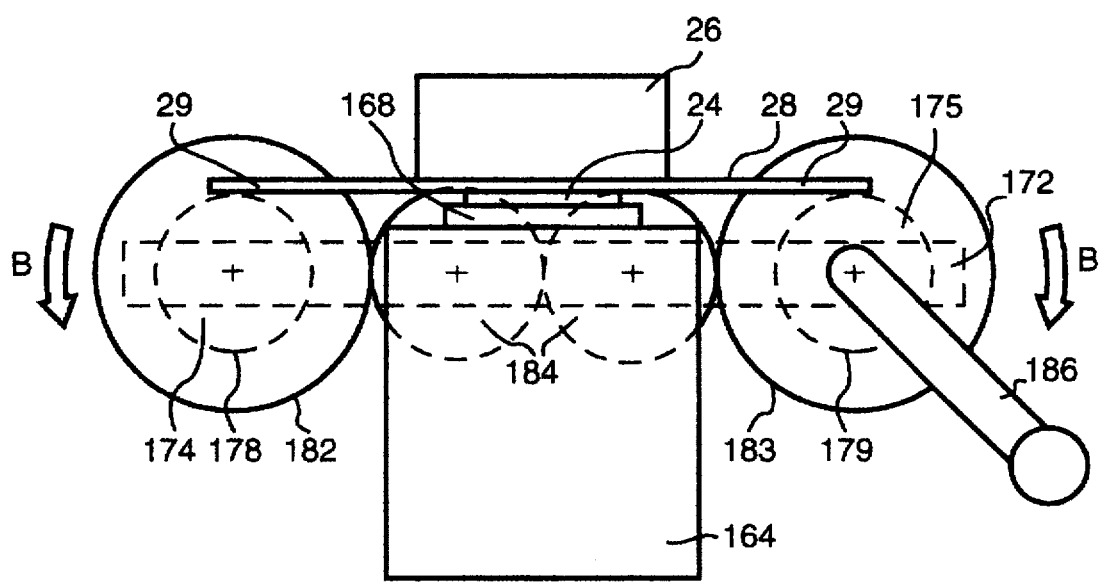

FIG. 10B illustrates the operation of the stretcher. The flow unit 20 is placed over the metal block 168 with substrate 24 in contact with the surface 170 so as to hold the substrate 24 in place by suction. The free ends 29 of the gasket 28 are secured on the wheels 174, 175. The crank 186 is then turned so as to rotate the wheels as indicated by the arrows B and thereby stretch the gasket 28 and separate it from the substrate 24. After the bond at the substrate-gasket interface 38 has been disrupted, the platen 26 and gasket 28 can be removed, the vacuum source turned off, and the substrate 24 lifted from the surface 170.

Figure 11:
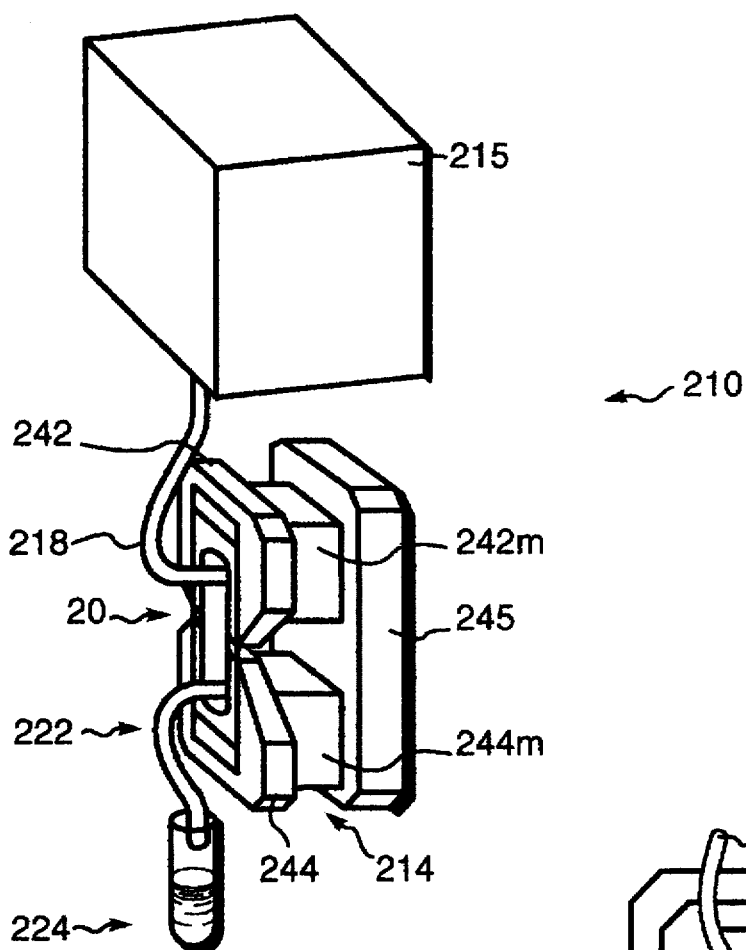
FIG. 11 depicts a single-channel analytical magnetic cell separator incorporating a flow unit of the invention.

FIG. 11 shows a Ferrograph, or an analytical magnetic cytometer "AMC") 210, with which the present invention may be used to advantage. The AMC 210 includes a flow unit, such as, for example, the flow unit 20 of FIGS. 1 and 2, mounted within a magnetic field established by a magnet structure 214. AMC 210 also has a fluid dispensing unit 215 for directing a bulk liquid along an entirely closed (i.e., sealed) fluidic pathway to an inlet tube 218, through the inlet channel 34, into flow unit 20, and then through the outlet channel 36 and the outlet tube 222. The outlet tube 222 directs spent bulk liquid from the flow unit 20 into a waste reservoir, e.g., a collection tube 224. The AMC 210 may include means for additionally directing a rinse fluid and a volume of gas, as described below, along an entirely closed fluidic pathway and into inlet tube 218.

Figure 12:
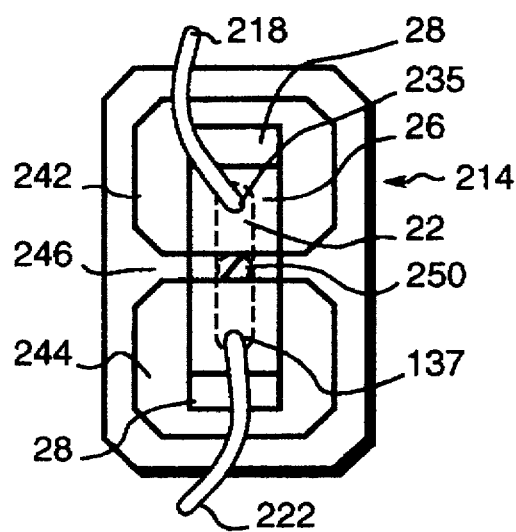
FIG. 12 is a front view of the flow unit and magnetic structure of FIG. 11.

The magnetic structure 214 has first and second magnetically permeable pole members 242, 244 separated by an interpolar gap 246 that is best seen in FIG. 12, and a magnetically permeable support member 245. Sandwiched between the pole members and support member 245 are first and second permanent magnets 242 m, 244 m. The interpolar gap 246 is, e.g., 1.25 mm wide and 75 mm long. The pole members 242, 244 establish a magnetic flux density at the interpolar gap 246 that can range up to the saturation point of the pole pieces, generally on the order of 2 Tesla.

As is shown in FIG. 12, the flow unit 20 is disposed in the AMC 210 so that the elongated flow chamber 22 extends perpendicularly across the interpolar gap 246 approximately mid-way along the chamber's length. The chamber 22 is disposed in a plane generally perpendicular to the opposed faces of pole members 242, 244, which define interpolar gap 246. It should be noted that the flow chamber 22 extends in the illustrated embodiment in a vertical direction. Vertical flow clearly separates the vertical force of gravity from the inward magnetic force, so that only the latter acts to retain magnetically tagged cells moving downwardly through flow chamber 22.

During operation of the AMC, the fluid dispensing system 215 directs the bulk fluid with suspended cells into the inlet tube 218, which is coupled to the inlet channel 34 in the platen 26 (FIG. 2) at the end 35 (i.e., the top end) of the chamber 22. The liquid passes, in a thin laminar layer (i.e., a layer having a laminar velocity profile), into the flow chamber 22 disposed in a magnetic field of strong gradient, localized adjacent to the gap 246 of the magnet 214. This field draws the labeled cells toward the substrate 24, on which they are deposited in a deposition area 250 (FIG. 12) of the flow chamber 22 that overlies the gap 246. The liquid leaves the flow chamber 22 through the outlet channel 36 at the end 37 (i.e., the bottom end) of the chamber 22, which is coupled to the outlet tube 222. The unlabeled cells are carried away from the magnetic region and into the collection tube 224.

If desired, the fluid dispensing system is then activated to allow a rinse fluid, and thereafter a gas, to enter the flow chamber 22 via the inlet tube 218 and pass across the deposited cellular material in the flow chamber 22. The gas drives off excess liquid, and the cells remain attached to the substrate 24 in deposition area 250. Rapid clearance of the liquid prevents cell lysis, which can result from the increasing ion concentrations that accompany evaporation of the liquid. The rate and efficiency of liquid clearance is assisted by the vertical orientation of flow chamber 22.

After the gas-injection step has been completed, the labeled cells in the deposition area 250 form a characteristic "signature" band based on relative magnetic susceptibilities. The flow unit 20 can then be disassembled. The substrate 24 with the deposited cells is now available for conventional cytochemical staining and microscopic observation. For example, the collected cells can be analyzed by optical methods (e.g., transmitted-light attenuation, polarized-light analysis, scattered-light intensity analysis), fixing and histological staining (including immunohistological stains) followed by light densitometry analysis, and microscopic observation using either light or fluorescence microscopy. As an alterative the collected cells can be re-suspended for further processing by removing the flow unit 20 from the magnet 214, disassembling the unit 20 as described hereinabove, and gently washing the cells from the substrate 24. Indeed, the collected cells can be alive, and cultures can be grown therefrom.

In order to perform simultaneous sorting of several portions of a bulk liquid, a multi-chambered flow unit, with a gasket such as 128 (FIG. 7), 146 (FIG. 8), or 150 (FIG. 9) is used. After assembly and loading into the AMC 210, each of the resulting flow chambers has equally sized rectangular flow deposition areas disposed over the interpolar gap 246, as shown in FIG. 12 for the single-chambered flow unit 20. The liquid is divided into separate aliquots, and a different cell subpopulation magnetically marked in each aliquot. Each aliquot is fed into a separate holding reservoir in the fluid dispensing system. Liquid is directed from each holding reservoir into a separate inlet tube 118 and inlet port in the platen. Alternatively, different holding reservoirs can be used to hold separate, independent samples (i.e., from different sources), which can be sorted simultaneously to save time. (Five concurrently run samples take only 20% of the time that the same five samples would take if run consecutively.)

This multi-chambered flow unit can be used to particular advantage where ratios of different subpopulations are required, because simultaneous sorting of multiple cell types from the same sample avoids interference from extraneous experimental variables (e.g., temperature- and time-dependent concentration changes) that could influence results if the different cell types were sorted serially, one after another.

It will therefore be seen that the foregoing represents a highly advantageous approach to forming a flow unit, especially for use in a Ferrograph. The possible uses of the invention set forth herein are but some that can be realized; others will be apparent to those skilled in the art. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A flow unit, adapted for flow of a liquid therethrough, having at least one chamber, the unit comprising:
   a. a transparent unapertured substrate having opposite edges and a flat surface;
   b. a platen, parallel to the substrate, having opposite edges and a flat surface and two communication channels therethrough, one communication channel being an inlet channel and the other communication channel being an outlet channel, each communication channel having a respective interior end at the flat surface of the platen; and
   c. a gasket, comprising a flexible portion having a chamber hole therethrough, the hole having opposite ends and opposite sides extending between the opposite ends, the flexible portion being interposed between the flat surfaces of the substrate and the platen and in contact therewith so as to form a liquid-tight seal around the hole, thereby forming a chamber, the interior ends of the communication channels being disposed over the chamber hole near the respective opposite ends thereof so as to allow flow of the liquid through the chamber, the gasket having a pair of opposite exposed free ends, separated by a length, that extend beyond the opposite edges of the substrate and of the platen so as to allow disassembly of the unit, without appreciably bending the substrate, by pulling the free ends in opposite directions parallel to the surface of the substrate and thereby stretching the flexible portion.

2. The flow unit of claim 1 wherein the substrate is a glass substrate.

3. The flow unit of claim 2 wherein the substrate has a thickness less than 150 micrometers.

4. The flow unit of claim 1 wherein the flexible portion of the gasket comprises at least one of silicone rubber and latex rubber.

5. The flow unit of claim 1 wherein each of the free ends comprises a relatively rigid portion, having lower elasticity than the flexible portion, coupled to the flexible portion and extending substantially across the free end in a direction perpendicular to the length separating the opposite free ends, so as to reduce the stretching required to disassemble the unit and to provide a substantially uniform stretching of the gasket across the free ends when the free ends are pulled.

6. The flow unit of claim 1 wherein the platen comprises a polymeric material.

7. The flow unit of claim 1 wherein the flexible portion of the gasket comprises two stress concentration holes therethrough, the stress concentration hole being positioned proximate the opposite sides of the chamber hole so that the opposite sides of the chamber hole move away from one another when the free ends of the gasket are pulled in opposite directions.

8. The flow unit of claim 1 wherein the gasket has a plurality of chamber holes therethrough, each chamber hole forming a distinct chamber with the substrate and the platen.

9. The flow unit of claim 1 wherein the chamber hole is elongated along said length.

10. The flow unit of claim 1 wherein the chamber hole is elliptical.

11. The flow unit of claim 1 wherein the flexible portion of the gasket has the property that the liquid does not wet it.

12. The flow unit of claim 1 wherein the flow unit is configured for use in a ferrograph.

13. A flow unit, adapted for flow of a liquid therethrough, having a plurality of chambers, the unit comprising:
   a. a glass substrate, less than 150 micrometers thick, having opposite edges and a flat surface;
   b. a platen, parallel to the substrate, having opposite edges and a flat surface and more than one pair of communication channels therethrough, each pair comprising an inlet channel and an outlet channel, each communication channel having a respective interior end at the flat surface of the platen; and
   c. a gasket, comprising a flexible portion having a plurality of elongated chamber holes therethrough, each of the holes having opposite ends and opposite sides extending between the ends, the flexible portion being disposed between the flat surfaces of the substrate and the platen and in contact therewith so as to form a liquid-tight seal around each of the chamber holes, thereby forming a plurality of chambers, respective interior ends of respective pairs of communication channels being disposed over respective chamber holes near the opposite ends thereof so as to allow flow of the liquid through each of the chambers from one end thereof to the other, the gasket having a pair of opposite exposed free ends, separated by a length, that extend beyond the opposite edges of the substrate and of the platen so as to allow disassembly of the unit, without appreciably bending the substrate, by pulling the free ends in opposite directions parallel to the surface of the substrate, thereby stretching the flexible portion.

14. The flow unit of claim 13 wherein each of the free edges comprises a relatively rigid portion, having lower elasticity than the flexible portion, coupled to the flexible portion, and extending substantially across the free end in a direction perpendicular to the length, so as to reduce the stretching required to disassemble the unit and to provide a substantially uniform stretching of the gasket across the free ends when the free ends are pulled.

15. The flow unit of claim 13 wherein the flexible portion of the gasket comprises two stress concentration holes therethrough, the stress concentration holes positioned proximate the opposite sides of a single chamber hole so that the opposite sides of the single chamber hole move away from one another when the free ends of the gasket are pulled in opposite directions.

16. The flow unit of claim 13 wherein the chamber hole is elongated along the length.

17. The flow unit of claim 13 wherein the flexible portion of the gasket has the property that the liquid does not wet it.

18. The flow unit of claim 13 wherein the flow unit is configured for use in a ferrograph.

19. An apparatus comprising:
   a. an unapertured substrate having opposite edges and a flat surface;
   b. a platen, parallel to the substrate, having opposite edges and a flat surface; and
   c. a gasket, comprising a flexible portion having a chamber hole therethrough, the hole having opposite ends and opposite sides extending between the ends, the flexible portion being interposed between the flat surfaces of the substrate and the platen and in contact therewith, so as to form a liquid-tight seal around the hole, thereby forming a chamber, the gasket having a pair of opposite exposed free ends extending beyond the opposite edges of the substrate and of the platen so as to allow disassembly of the unit, without appreciably bending the substrate, by pulling the free ends in opposite directions parallel to the surface of the substrate, thereby stretching the flexible portion.

20. The apparatus of claim 19 wherein the chamber has an interior and an exterior and the platen has a communication channel therethrough, the channel having an interior end at the flat Surface of the platen and an exterior end, the interior end being disposed over the chamber hole so as to allow communication of the interior of the chamber with the exterior thereof.

21. The apparatus of claim 19 wherein the substrate is a glass substrate.

22. The apparatus of claim 21 wherein the substrate is less than 150 micrometers thick.

* * * * *